Sept. 23, 1947. J. C. RUTENSCHROER Plant Pat. 763
NEPHTHYTIS PLANT
Filed Nov. 25, 1946
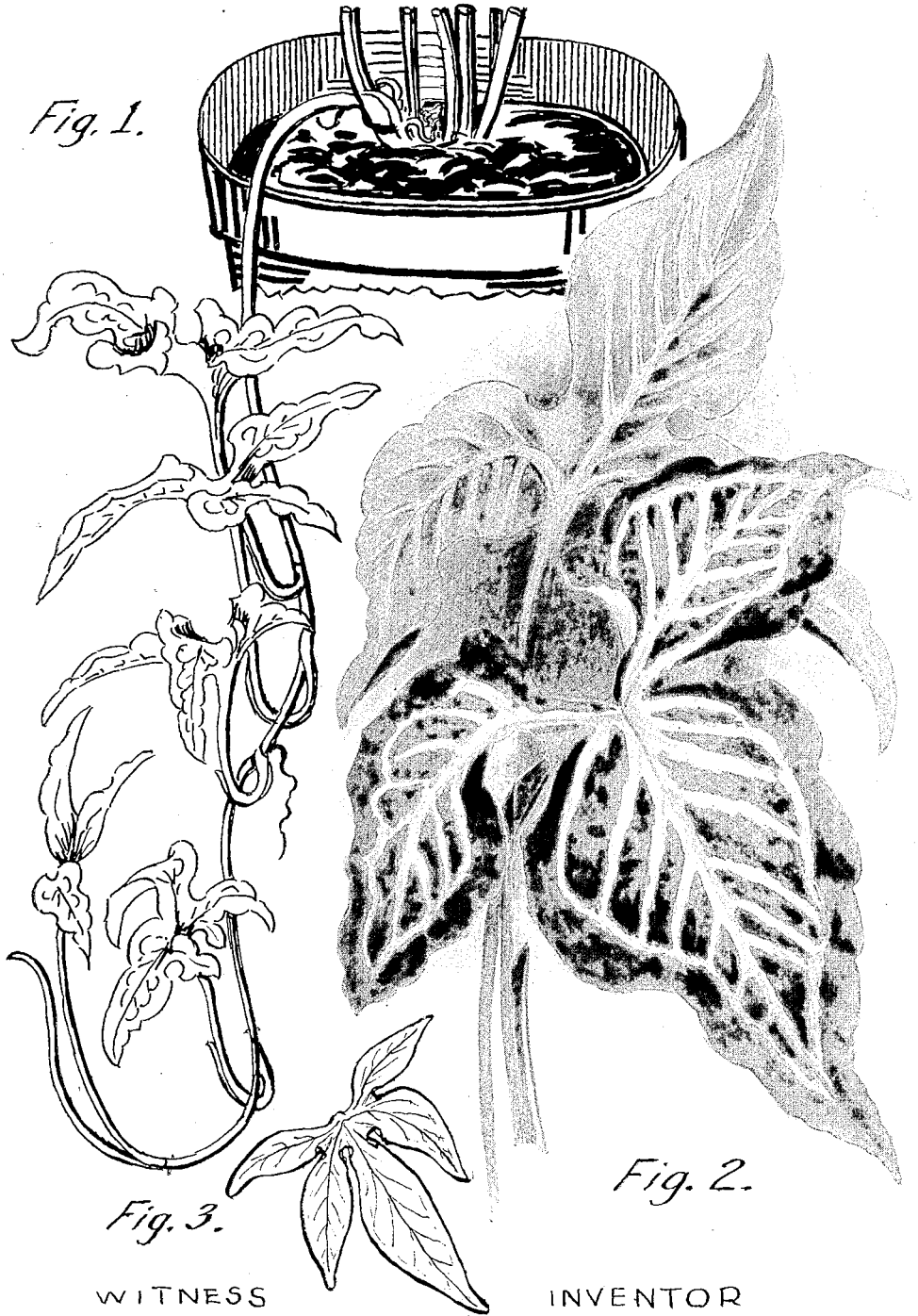
WITNESS
Addison J. Avery
INVENTOR
JOHN C. RUTENSCHROER,
by Rummler Rummler & Davis,
ATTYS.

Patented Sept. 23, 1947

Plant Pat. 763

UNITED STATES PATENT OFFICE

763

NEPHTHYTIS PLANT

John C. Rutenschroer, Cincinnati, Ohio

Application November 25, 1946, Serial No. 712,131

1 Claim. (Cl. 47—59)

This new variety of Nephthytis plant, herein described and illustrated, was a sport on a Nephthytis, liberica plant discovered by me about three years ago. This new variety has been asexually reproduced by cuttings and its characteristics appear to be permanently fixed. At the present time there are 2700 plants in existence at a greenhouse in Cincinnati, Ohio.

The parent Nephthytis, liberica plant has a single hastate or arrow-shaped leaf at the apex of each long petiole. This leaf is an all-over, medium green in color with no marked variegated coloring showing of the veins.

This new variety is distinctly and outstandingly different from the parent variety both with respect to its leaf coloring and formation, particularly the peculiar lobation and fluting of the leaves, whereby some have the appearance of trifoliate and some of quinquefoliate compound leaves.

To establish these novel and unique characteristics was the primary object of this invention. The new plant grows vigorously and thrives as a house plant.

In the accompanying illustration Figure 1 is a fragmentary pen sketch indicating the herbaceous nature of the growth and shows a vine-like runner in detail. Fig. 2 shows the form and coloring of the leaves in natural tints. The upper portion of the view shows the under side of a leaf and the lower portion shows the top side of a three-bladed leaf. Fig. 3 is a top view showing the shape of a five-bladed leaf on a much reduced scale.

Referring to the general structure of this new variety, it is an herbaceous plant with long petioled, arrow-shaped, sharp-pointed leaves, comprising three or five blades radiating horizontally from the top of a single petiole branching from a segmented stem. The flowers are borne on a nearly erect cylindrical spadix, the spathe being decurrent on the peduncle. These are omitted from the drawing as the distinctive novelty resides in the leaf markings and leaf structure. The petioles are very sturdy, some growing very straight while others bend gracefully outward from the main stem. The petioles spring from nodal joints in the stem and have sheathlike basal portions that embrace the stem above the node for a short distance so that the curvature of the petioles is tangent to the stem. The leaves are of a substantial quality, firm and leathery. In the mature three-bladed leaf, the middle blade is approximately 5 inches long and 3 inches wide, while the two smaller diverging blades are approximately 3¼ inches long by 1½ inches wide.

The blades of the leaf are separated by deep marginal incisions or bays so that they have the appearance of being separate leaves, but they are connected by ruffled web portions that are conically folded and bowed upward or downward so as to draw the side blades forward toward the central blade.

In the five-bladed leaves, which occur on the same plant with the three-bladed leaves, the marginal bays separating the blades are much deeper than in the three-bladed leaves and the ruffled web portions are smaller but similarly bowed. In each form of leaf, each blade has a central vein with divergently branching veins in herring-bone arrangement that are merged into a marginal vein spaced inward from the marginal rim of the blade. These veins appear as projecting ribs on the underside of the leaf and as grooves on the upper surface of the leaf. The veins are marked by whitish variegations in the color of the leaf on its upper side. The petioles average about 8 inches in height. Each petiole has a fin-like leaf formation going part way up from its joint with the stem, which adds to its beauty.

The color characteristics of my new variety according to Maerz and Paul Dictionary of Color are shown in the following table:

| | Plate | Letter | No. |
|---|---|---|---|
| Body color of face of leaf | 22 | L | 10 |
| Lightest color of markings on main veins to outer border | 18 | H | 4 |
| Back of leaf | 21 | L | 7 |
| Heavy under ribs | 21 | K | 5 |
| Petiole | 21 | L | 9 |
| Fin on petiole of leaf | 7 | A | 10 |

The novel characteristics reside in the three-bladed and five-bladed forms of the individual leaves, the white colored central vein with white branching veins, and the very distinct border vein paralleling the periphery of the leaf. All the veins on the leaf appear as grooves in the upper surface of the leaf and form deep semi-cylindrical ridges on the bottom surface. The central rib divides the leaf almost exactly in two and forms a straight line down to the unveined marginal border which is about ¼ inch wide. The branching veins also extend to and merge into this marginal border. This border has the general effect of being stitched on to the leaf. The older leaves are a deeper green than the newer ones. Thus the plant has a pleasing effect of light and dark green tones, combined with the pronounced white markings of conventional design and a distinctively novel leaf structure.

When this new variety is about eight months old it has a vining or runner-forming tendency. The vine growth lends itself to growth on totem poles and other supports for ornamental display.

This new variety is an indoor plant with good keeping qualities and well suited for use either as a potted plant or as a "dish" plant. It will live in water alone; thus overwatering does not harm it. Its comparatively small size, conspicuous coloring and adaptability as a pot or dish plant combine to make this variety stand out as a distinctive commercial product.

Having thus disclosed the invention, I claim:

A new and distinct variety of Nephthytis plant as herein shown and described, characterized as to novelty by the trifoliate and quinquefoliate form of the individual leaves; the white markings of the veins; the distinctive border marking near the periphery of each leaf; and the ruffled web formation between blades of the leaf.

JOHN C. RUTENSCHROER.